US00PP27372P2

(12) United States Plant Patent
Arisumi et al.

(10) Patent No.: US PP27,372 P2
(45) Date of Patent: Nov. 15, 2016

(54) ***TECOMA* PLANT NAMED 'SUNHORTEAKA'**

(50) Latin Name: *Tecoma hybrida*
Varietal Denomination: Sunhorteaka

(71) Applicants: Kenichi Arisumi, Kagoshima (JP); Yasuo Kobayashi, Fukuoka (JP)

(72) Inventors: Kenichi Arisumi, Kagoshima (JP); Yasuo Kobayashi, Fukuoka (JP)

(73) Assignee: Suntory Flowers Limited, Tokyo (JP)

( * ) Notice: Subject to any disclaimer, the term of this patent is extended or adjusted under 35 U.S.C. 154(b) by 117 days.

(21) Appl. No.: 14/544,309

(22) Filed: Dec. 20, 2014

(51) Int. Cl.
*A01H 5/02* (2006.01)

(52) U.S. Cl.
USPC ..... Plt./226

(58) Field of Classification Search
USPC ..... Plt./226
See application file for complete search history.

*Primary Examiner* — Anne Grunberg
(74) *Attorney, Agent, or Firm* — C. A. Whealy

(57) ABSTRACT

A new and distinct cultivar of *Tecoma* plant named 'Sunhorteaka', characterized by its semi-upright plant habit; vigorous growth habit; early and freely flowering habit; flowering under high temperature conditions; orange red, vivid orange and vivid reddish yellow-colored flowers; and low temperature tolerance.

1 Drawing Sheet

Botanical designation: *Tecoma hybrida.*
Cultivar denomination: 'SUNHORTEAKA'.

CROSS REFERENCED TO CLOSELY-RELATED APPLICATIONS

Title: *Tecoma* Plant Named 'Sunhorteki'
Applicants: Kenichi Arisumi & Yasuo Kobayashi
Filed: Concurrently with this application having Plant patent application Ser. No. 14/544,310

BACKGROUND OF THE INVENTION

The present invention relates to a new and distinct cultivar of *Tecoma* plant, botanically known as *Tecoma hybrida* and hereinafter referred to by the name 'Sunhorteaka'.

The new *Tecoma* plant is a product of a planned breeding program conducted by the Inventors in Chikushino-shi, Fukuoka, Japan. The objective of the breeding program is to create new early and freely flowering *Tecoma* plants with low temperature tolerance.

The new *Tecoma* plant originated from a cross-pollination in Chikushino-shi, Fukuoka, Japan in May, 2009 of a proprietary selection of *Tecoma hybrida* identified as code name Horteco-1, not patented, as the female, or seed parent with a proprietary selection of *Tecoma hybrida* identified as code name Horteco-2, not patented, as the male, or pollen, parent. The new *Tecoma* plant was discovered and selected by the Inventors as a single flowering plant from within the progeny of the stated cross-pollination in a controlled greenhouse environment in Chikushino-shi, Fukuoka, Japan in July, 2009.

Asexual reproduction of the new *Tecoma* plant by cuttings in Chikushino-shi, Fukuoka, Japan since August, 2009 has shown that the unique features of this new *Tecoma* plant are stable and reproduced true to type in successive generations.

SUMMARY OF THE INVENTION

Plants of the new *Tecoma* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunhorteaka'. These characteristics in combination distinguish 'Sunhorteaka' as a new and distinct *Tecoma* plant:

1. Semi-upright plant habit.
2. Vigorous growth habit.
3. Early and freely flowering habit.
4. Flowering under high temperature conditions.
5. Orange red, vivid orange and vivid reddish yellow-colored flowers.
6. Low temperature tolerant.

Plants of the new *Tecoma* can be compared to plants of the female parent selection. Plants of the new *Tecoma* differ primarily from plants of the female parent selection in the following characteristics:

1. Plants of the new *Tecoma* flower earlier than plants of the female parent selection.
2. Plants of the new *Tecoma* flower under high temperature conditions whereas plants of the female parent selection do not typically flower under high temperature conditions.
3. Plants of the new *Tecoma* are more low temperature-tolerant than plants of the female parent selection.

Plants of the new *Tecoma* can be compared to plants of the male parent selection. Plants of the new *Tecoma* differ primarily from plants of the male parent selection in the following characteristics:

1. Plants of the new *Tecoma* flower earlier than plants of the male parent selection.
2. Plants of the new *Tecoma* and the male parent selection differ in flower color as plants of the male parent selection have reddish yellow-colored flowers.
3. Plants of the new *Tecoma* flower under high temperature conditions whereas plants of the male parent selection do not typically flower under high temperature conditions.

4. Plants of the new *Tecoma* are more low temperature-tolerant than plants of the male parent selection.

Plants of the new *Tecoma* can be compared to plants of *Tecoma hybrida* 'Sunhorteki', disclosed in a U.S. Plant patent application Ser. No. 14/544,310. Plants of the new *Tecoma* differ primarily from plants of 'Sunhorteki' in flower color as plants of 'Sunhorteki' have bright yellow-colored flowers.

Plants of the new *Tecoma* can also be compared to plants of the *Tecoma* 'Mayan Gold', not patented. In side-by-side comparisons conducted in Higashiomi, Shiga, Japan, plants of the new *Tecoma* differed from plants of 'Mayan Gold' in the following characteristics:

1. Plants of the new *Tecoma* were smaller than plants of 'Mayan Gold'.
2. Plants of the new *Tecoma* had larger leaves than plants of 'Mayan Gold'.
3. Plants of the new *Tecoma* were more freely flowering than plants of 'Mayan Gold'.
4. Plants of the new *Tecoma* had smaller flowers than plants of 'Mayan Gold'.
5. Plants of the new *Tecoma* and 'Mayan Gold' differed in flower color as plants of 'Mayan Gold' had bright yellow-colored flowers.

BRIEF DESCRIPTION OF THE PHOTOGRAPHS

The accompanying colored photographs illustrate the overall appearance of the new *Tecoma* plant showing the colors as true as it is reasonably possible to obtain in colored reproductions of this type. Colors in the photographs may differ slightly from the color values cited in the detailed botanical description which accurately describe the actual colors of the new *Tecoma* plant.

The photograph at the top of the sheet comprises a side perspective view of a typical flowering plant of 'Sunhorteaka' grown in a container.

The photograph at the bottom of the sheet is a close-up view of a typical inflorescence of 'Sunhorteaka'.

DETAILED BOTANICAL DESCRIPTION

The aforementioned photographs and following observations, measurements and values describe plants grown during the late spring in 15-cm containers in an outdoor nursery in Higashiomi, Shiga, Japan and under cultural practices typical of commercial *Tecoma* production. During the production of the plants, day temperatures averaged 28° C. and night temperatures averaged 23° C. Plants were ten months old when the photographs and detailed description were taken. In the following description, color references are made to The Royal Horticultural Society Colour Chart, 2007 Edition, except where general terms of ordinary dictionary significance are used.

Botanical classification: *Tecoma hybrida* 'Sunhorteaka'.

Parentage:

*Female, or seed, parent*.—Proprietary selection of *Tecoma hybrida* identified as code name Horteco-1, not patented.

*Male, or pollen, parent*.—Proprietary selection of *Tecoma hybrida* identified as code name Horteco-2, not patented.

Propagation:

*Type*.—By vegetative cuttings.

*Time to initiate roots, summer*.—About 20 days at temperatures about 25° C. to 30° C.

*Time to initiate roots, winter*.—About 35 days at temperatures about 18° C. to 23° C.

*Time to produce a rooted young plant, summer*.—After root initiation, about 15 days at temperatures about 25° C. to 30° C.

*Time to produce a rooted young plant, winter*.—After root initiation, about 25 days at temperatures about 15° C. to 20° C.

*Root description*.—Fibrous; white in color.

*Rooting habit*.—Freely branching.

Plant description:

*Plant and growth habit*.—Upright to somewhat outward plant habit; vigorous growth habit.

*Plant height*.—About 26 cm.

*Plant width (or plant spread)*.—About 27.8 cm.

*Lateral branch description*.—Length: About 18.8 cm. Diameter: About 2.7 mm. Internode length: About 3.3 cm. Strength: Strong. Texture: Smooth, glabrous. Color, developing: Close to 144C. Color, woody: Close to N199A.

Leaf description:

*Arrangement*.—Opposite; pinnately compound with three or five leaflets per leaf.

*Leaf length*.—About 15.1 cm.

*Leaf width*.—About 9.2 cm.

*Terminal leaflet length*.—About 7.9 cm to 10.2 cm.

*Terminal leaflet width*.—About 3.2 cm to 4.4 cm.

*Lateral leaflet length*.—About 5 cm to 6.9 cm.

*Lateral leaflet width*.—About 1.9 cm to 4.3 cm.

*Leaflet shape*.—Elliptic to narrowly elliptic.

*Leaflet apex*.—Acuminate.

*Leaflet base*.—Cuneate.

*Leaflet margin*.—Shallowly serrate.

*Leaflet texture, upper and lower surfaces*.—Smooth, glabrous.

*Leaflet venation pattern*.—Pinnate, reticulate.

*Leaflet color*.—Developing leaflets, upper surface: Close to 144A. Developing leaflets, lower surface: Close to 144B. Fully expanded leaflets, upper surface: Close to 137B; venation, close to N144B. Fully expanded leaflets, lower surface: Close to 138A; venation, close to 144D.

*Leaf petioles*.—Length: About 4.4 mm. Diameter: About 1.3 mm. Texture, upper and lower surfaces: Smooth, glabrous. Color, upper and lower surfaces: Close to 144A.

*Terminal leaflet petioles*.—Length: About 2.1 mm. Diameter: About 1.8 mm. Texture, upper and lower surfaces: Smooth, glabrous. Color, upper and lower surfaces: Close to 144A.

*Lateral leaflet petioles*.—Length: About 2.8 mm. Diameter: About 1.9 mm. Texture, upper and lower surfaces: Smooth, glabrous. Color, upper and lower surfaces: Close to 144A.

Flower description:

*Flower type and habit*.—Single salverform flowers arranged in terminal panicles; flowers face upright to outwardly; freely flowering habit with about 14 flowers per inflorescence and about two to three inflorescences developing per plant.

*Natural flowering season*.—Early flowering habit, plants flower in mid-May and towards the end of September in Japan; plants begin flowering about six to nine weeks after planting.

*Flower longevity*.—Flowers last about two to three days on the plant; flowers not persistent.

*Fragrance*.—Slightly fragrant, pleasant.

*Inflorescence height*.—About 8.9 cm.

*Inflorescence diameter*.—About 9 cm.

*Flower buds*.—Height: About 3.4 cm. Diameter: About 7.7 mm. Shape: Club-shaped. Color: Towards the apex, close to N34A; towards the base, close to 8B.

*Flowers*.—Appearance: Salverform; flared trumpet, corolla fused and five-parted. Diameter: About 3.3 cm. Depth (length): About 2.9 cm. Throat diameter: About 1.1 cm. Tube length: About 4.3 cm. Tube diameter: About 9.3 mm.

*Corolla*.—Quantity and arrangement: Five petals arranged in a single whorl and fused towards the base into an elongated tube. Petal lobe shape: Orbicular. Petal lobe apex: Rounded; occasionally emarginate. Petal lobe margin: Entire. Petal lobe texture, upper and lower surfaces: Smooth, glabrous. Throat texture: Smooth, slightly pubescent. Tube texture: Smooth, glabrous. Color: Petal lobe, when opening, upper and lower surfaces: Close to 34A to 34B. Petal lobe, fully opened, upper surface: Close to N34A, N25C and 16A. Petal lobe, fully opened, lower surface: Close to 26B and 16A. Throat: Close to 12A; thin stripes, close to 33B. Tube: Close to 42B and 12A.

*Calyx*.—Quantity and arrangement: Five sepals arranged in a single whorl, fused at the base. Sepal length: About 1.4 mm. Sepal width: About 0.9 mm. Sepal shape: Triangular. Sepal apex: Acute. Sepal margin: Entire. Sepal texture, upper and lower surfaces: Smooth, glabrous. Sepal color: When developing and fully opened, upper surface: Close to 144B tinted with close to 173A. When developing and fully opened, lower surface: Close to 144C.

*Peduncles*.—Length: About 4.6 cm. Diameter: About 1.6 mm. Texture: Smooth, glabrous. Aspect: Upright to somewhat outwardly. Color: Close to 144A.

*Pedicels*.—Length: About 5.3 mm. Diameter: About 1.3 mm. Texture: Smooth, glabrous. Aspect: Semi-upright. Color: Close to 144B.

*Reproductive organs*.—Stamens: Quantity per flower: Typically four. Stamen length: About 2.2 cm. Anther shape: Variable. Anther color: Close to 10C. Filament color: Close to 1D. Pollen amount: None observed. Pistils: Quantity: Typically one. Pistil length: About 4.3 cm. Style color: Close to 145D. Stigma shape: Spatulate, bi-parted. Stigma color: Close to 145C. Ovary color: Close to 144B.

*Seeds and fruits*.—Seed and fruit production have not been observed on plants of the new *Tecoma*.

Disease & pest resistance: Plants of the new *Tecoma* have not been noted to be resistant to pathogens and pests common to *Tecoma* plants.

Garden performance: Plants of the new *Tecoma* have been observed to tolerate wind, rain and temperatures ranging from about −5° C. to about 35° C.

It is claimed:

1. A new and distinct *Tecoma* plant named 'Sunhorteaka' as illustrated and described.

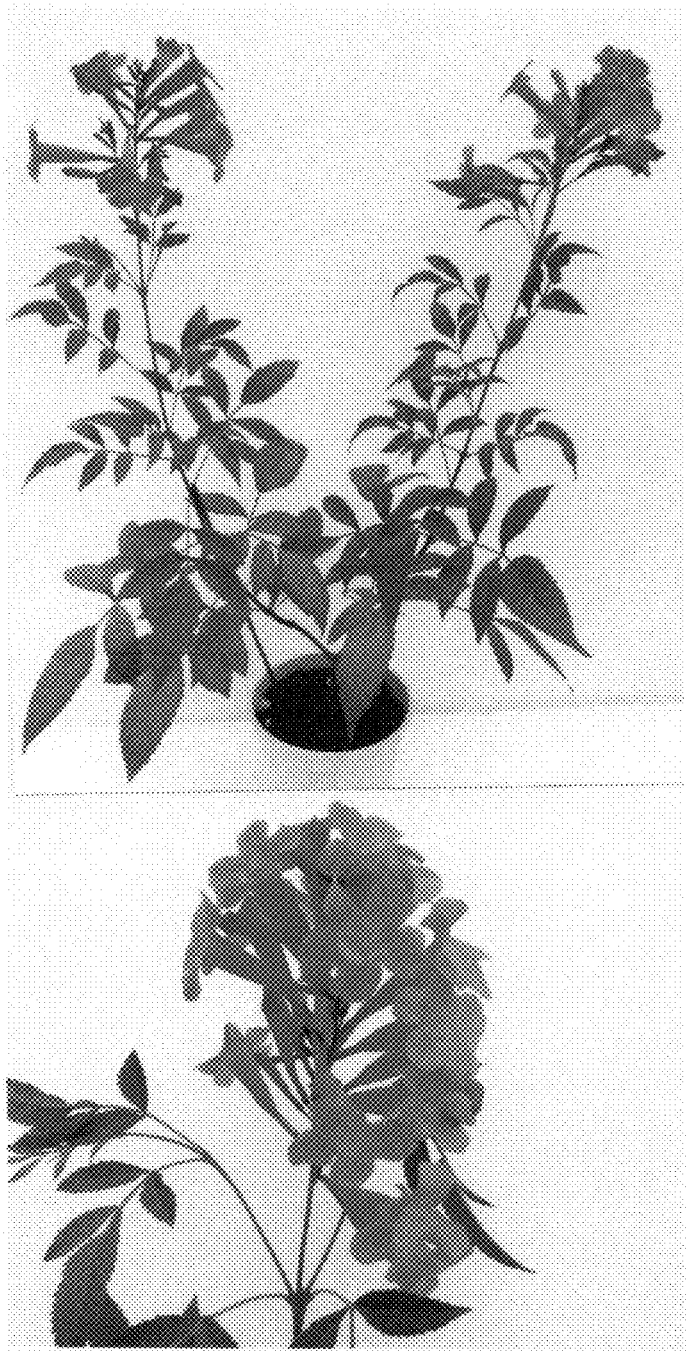

* * * * *